(12) United States Patent
Mielnik et al.

(10) Patent No.: US 9,594,079 B2
(45) Date of Patent: Mar. 14, 2017

(54) PROTEIN SPECIFIC OPTICAL DETECTION

(71) Applicant: Sinvent AS, Trondheim (NO)

(72) Inventors: Michal Marek Mielnik, Jar (NO); Jon Olav Grepstad, Oslo (NO); Ib-Rune Johansen, Oslo (NO)

(73) Assignee: Sinvent AS, Trondheim (NO)

( * ) Notice: Subject to any disclaimer, the term of this patent is extended or adjusted under 35 U.S.C. 154(b) by 240 days.

(21) Appl. No.: 14/420,023

(22) PCT Filed: Aug. 13, 2013

(86) PCT No.: PCT/EP2013/066880
§ 371 (c)(1),
(2) Date: Feb. 6, 2015

(87) PCT Pub. No.: WO2014/026968
PCT Pub. Date: Feb. 20, 2014

(65) Prior Publication Data
US 2015/0219642 A1 Aug. 6, 2015

(30) Foreign Application Priority Data
Aug. 16, 2012 (NO) .................................. 20120916

(51) Int. Cl.
| G01N 31/00 | (2006.01) |
| G01N 33/53 | (2006.01) |
| G01N 33/543 | (2006.01) |
| B82Y 20/00 | (2011.01) |
| G01N 21/77 | (2006.01) |
| G01N 21/47 | (2006.01) |

(52) U.S. Cl.
CPC ........ G01N 33/54366 (2013.01); B82Y 20/00 (2013.01); G01N 21/77 (2013.01); G01N 21/7743 (2013.01); *G01N 21/4788* (2013.01); *G01N 2021/7763* (2013.01); *G01N 2021/7773* (2013.01); *G01N 2021/7789* (2013.01)

(58) Field of Classification Search
CPC ........ G01N 21/05; G01N 21/45; G01N 21/77; G01N 33/53; G02B 6/122; B82Y 20/00
See application file for complete search history.

(56) References Cited

U.S. PATENT DOCUMENTS

2008/0278722 A1   11/2008   Cunningham et al.
2009/0079976 A1    3/2009   Cunningham et al.

FOREIGN PATENT DOCUMENTS

WO    WO-2010108952 A1    9/2010

OTHER PUBLICATIONS

Grepstad, Jon Olav et al.; "Enhanced Scattering from Nano-Particles Trapped in Photonic Crystal Membranes"; Optical Mems and Nanophotonics (OMN), 2012 IEEE International Conference; Aug. 6, 2012; pp. 21-22.
Berg, JM et al.; "Section 4.3: Immunology Provides Important Techniques with Which to Investigate Proteins"; Biochemistry, 5th Edition; 2002; 7 pages.
Grepstad, Jon Olav et al.; "Photonic-Crystal Membranes for Optical Detection of Single Nano-Particles, Designed for Biosensor Application"; Optics Express, vol. 20, No. 7; Mar. 26, 2012; 12 pages.
Consalvo, Daniela, "International Search Report," prepared for PCT/EP2013/066880, as mailed Oct. 11, 2013, four pages.

Primary Examiner — Lisa Cook
(74) Attorney, Agent, or Firm — Winstead PC

(57) ABSTRACT

This invention relates to a system and method for detecting target molecules using an optical sensor element including a photonic crystal constituted by a membrane of a chosen transparent material, being provided with a number of defined openings in a chosen pattern, a chosen number of the openings providing capture molecules having a high affinity to target molecules, the pattern being adapted to provide resonance at a chosen wavelength, or range of wavelengths. The system and method also moving a first fluid flow containing target molecules through the openings and after this conducting a second fluid flow containing a second reactant being different from the capture molecules but having a high affinity for the target molecules but a low affinity for other possible molecules in the first flow. By illuminating the sensor element at a chosen wavelength thus obtaining a resonance and imaging means for providing an image of the sensor element it is possible to detect tight leaking from the resonator. Analyzing means may then detect the captured molecules as well as the reactant having reacted with them based on the amount of light leaking from the resonator.

6 Claims, 3 Drawing Sheets

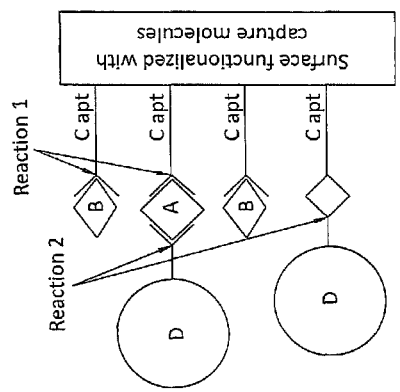
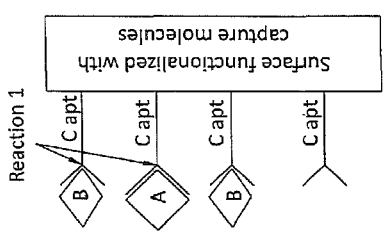
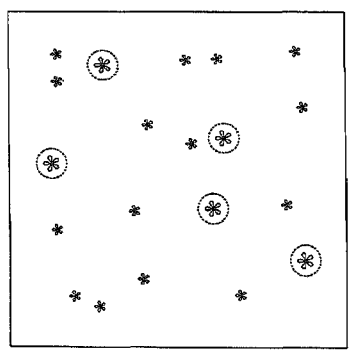
Fig. 4
Fig. 3

PROTEIN SPECIFIC OPTICAL DETECTION

This application is a continuation of 371 PCT/EP2013/066880 filed Aug. 13, 2013 and foreign application number 20120916 filed on Aug. 16, 2012 in Norway. Both of which are incorporated herein by reference.

INTRODUCTION

This invention relates to an optical sensor element comprising a photonic crystal constituted by a membrane of a chosen transparent material, and more specifically the membrane being provided with a number of defined openings (pores) in a chosen pattern, the pattern being adapted to provide resonance at a chosen wavelength or range of wavelengths.

The detector can detect and spatially locate nano-particles. The sensing unit in the device can potentially be chemically functionalized to capture macromolecules such as e.g. proteins and nucleic acids (RNA. DNA), exosomes viruses, and other bioparticles and biomarkers in human samples such as blood, saliva, urine, tissue samples, and others. The device can hence be used as a biosensor, applied both in vivo and in vitro Additionally, the device can be used to analyse other, non-medical sample types such as e.g. water and food. The photonic crystal and measuring principle as such is described in WO2010/0108952.

In medical diagnostics, where the main goal is to detect and identify (and quantify, if possible) biomarkers, both the sensitivity and the specificity of the biosensor are of high importance. The sensitivity of a biosensor is defined as the sensor's ability to avoid false negatives, while the specificity is its ability to avoid false positives. Under this definition, a sensor with 100% sensitivity will identify all true positive samples as positive. How many negative samples the sensor identifies as positive (i.e. false positive) is irrelevant with respect to the definition of sensitivity. As a limiting case, a sensor which identifies ALL samples as positive has 100% sensitivity because it does not have any false negatives (i.e. it does not miss any positive samples). Similarly, a sensor with 100% specificity will identify all true negative samples as negative. Again, how many positive samples it identifies as negative (false negative) is irrelevant with respect to the definition of specificity. As a limiting case, a sensor which identifies ALL samples as negative has 100% specificity because it does not have any false positives.

In a typical sample of interest there can be millions of different bioparticles (e.g. proteins), only a few of which are targeted by the biosensor. Many of them are similar. It is therefore not possible to make capture-molecules which react exclusively with the targeted proteins and no others. Even for a capture site with very high selectivity (i.e. very high affinity to target proteins and very low affinity to other proteins and bioparticles) there is some probability of binding a non-targeted protein to the sensor. In the case of a sample containing a very large number of non-targeted proteins compared to the number of targeted proteins, capturing of some non-targeted particles is therefore inevitable, consequently giving rise to false positives which in turn lowers the specificity of the sensor.

The object of the present invention is to provide a method for improving the specificity of the sensor. This object is obtained by a method according to the present invention, specified as stated in the accompanying claims.

Thus the present invention provides means for spatially locating nano-particles in combination with image processing. The biochemical means and active molecules may be based on the well known Enzyme-linked immunosorbent assay (ELISA) or similar methods.

The invention will be discussed more in detail below, with reference to the accompanying drawings, illustrating the invention by way of examples.

FIG. 3 illustrates the image intensity on a CCD screen as recorded after the first step.

FIG. 4 illustrates the steps according to the invention

FIG. 1 illustrates the sensor element used for performing the method according to the invention based on a photonic crystal unit as described in WO2010/108952. The following present invention being performed in order to increase the specificity of the measurements compared to the known solution being illustrated in FIG. 2.

Figure 2:
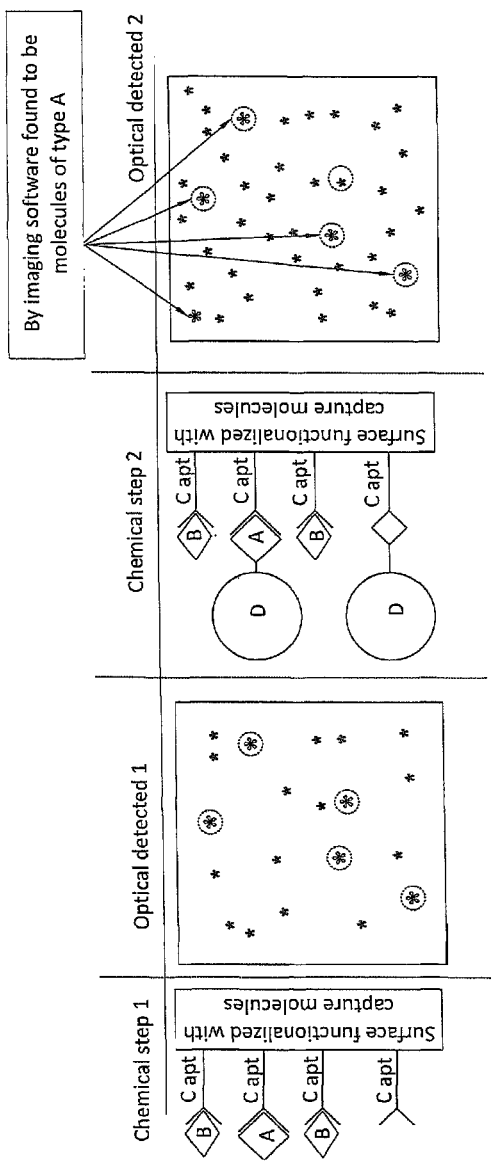
FIG. 2 illustrates the two chemical and optical detection steps that will increase specificity.

In FIG. 2 a chemical process is illustrated where the target molecules A are captured as well as some unwanted molecules B. In the optically detected image dashed circles mark the captured target molecules (true positives), while the rest of the bright spots are unwanted captured molecules (false positives). The reactants on the surface (the capture molecules) capturing the target molecules are named C.

The illustrated process may be described as comprising the following steps:

Step 1 Capture target molecules A chemically in the photonic crystal sensor by a functionalized surface (molecule C) with high affinity to target molecules and low affinity to all other molecules.

Step 2 Record an image of the photonic crystal sensor (by e.g. a CCD camera) containing the captured nano-particles. Captured particles are represented by bright spots in the image.

Step 3 Introduce a second capture molecule D with high affinity to the target molecule and low affinity to all other molecules.

Step 4 Record another image of the photonic crystal sensor. The sensing sites where molecule D has been captured will now stand out in brightness. Do image processing to find and count the target molecules (type A).

In addition to the described steps a number of washing steps are required.

DETAIL DESCRIPTION

Figure 1:
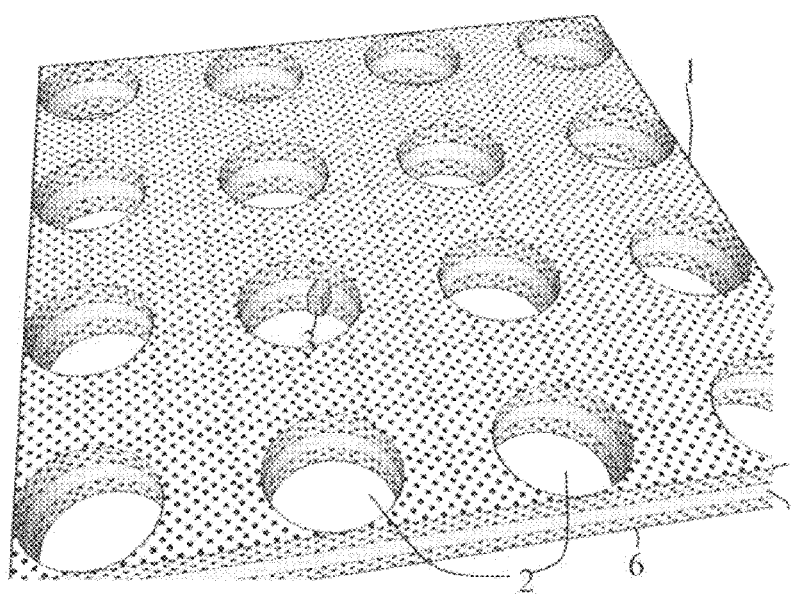
FIG. 1 illustrates the sensor element according to the known art used according to the invention.

Referring to FIG. 1 the process may be starting with a number $N_A$ of molecules A. They bind to a specific capture molecule C with likelihood $P_{CA}$. The likelihood P (i.e $P_{CA}$) may be defined in several ways, i.e. the total likelihood for a capture within one hole (defined openings), where the number of capture molecules can be N, N=1, 2, 3, . . . . Furthermore, all other molecules are labeled B and it is known that there is also a likelihood $P_{CB}$ for a molecule of type B to bind to C. Let the number of molecules of type B be $N_B$. As mentioned above the chemical step 1 is illustrated on the left side of FIG. 2 together with the resulting image of the sensor element.

It is reasonable to assume that $P_{CA}$ can be made much larger than $P_{CB}$. However, in real samples, the substance to be detected may be a minority population. $N_B$ can for example be $10^6$, while $N_A=10^2$. If $P_{CA}=90\%$ and $P_{CB}=0.1\%$, the number of captured molecules that are non-targeted (B) can hence be much larger ($10^6 \times 0.001=10^3$) than the number of captured target (A) molecules ($10^2 \times 0.9=90$)

In the example given here, the total number of captured molecules is on average $$M_{tot}=P_{CA}N_A+P_{CB}N_B=M_A+M_B=90+1000$$

In the above mentioned sensor device, all these 1090 molecules appear as bright spots on a dark background, as illustrated in FIG. 3. In the FIG. 3, dashed circles mark the target proteins (A). The other bright spots represent molecules of type B captured by the biosensor. At this stage, it is not possible to distinguish between the type A target molecules captured with probability $P_{CA}$ and the type B non-target molecules captured with probability $P_{CB}$. The biosensor detects a large number of false positives and hence exhibits low specificity.

Improvement of sensor specificity can be achieved as illustrated in FIG. 4, showing a two step reaction. In the first step, both molecules type A (blue molecules) and B (orange) bind to the capture molecules (C) with probabilities $P_{CA}$ and $P_{CB}$. The probability of binding type B molecules to the capture molecule is, as mentioned above, very low compared to the probability of binding molecules A. However, since there are many more type B molecules than type A molecules, more type B molecules end up being captured than molecules of type A.

At this point, the imaged biosensor appears as shown in FIG. 3, with no possibility to distinguish between type A (target) and type B (non-target) molecules. Referring to FIG. 3, in order to separate A and B molecules, a second step is introduced. This is a new reaction, introducing a fourth molecule, D, represented by the legged yellow sphere. D is selected or synthesized such that it has high affinity to the target molecule A, and low affinity to the non-target molecules B. Assume that the capture probability of D to A is $P_{AD}$=90%, and the capture probability of D to B is $P_{BD}$=0.1%. In addition, we note that D can react and bind directly to the capture molecules, C, at the red surface. Let us assume that this reaction has a probability $P_{CD}$=0.1%.

Imagine now that we start out with molecules of type A (target molecules) and molecules of type B (non-target molecules), and in the second step add molecules of type D (tag). In the first reaction step, 90 molecules of type A and 1000 molecules of type B are captured. In the second reaction step, we will on average be left with 81 stacks of C+A+D, 1 stack of C+B+D and 1000 stacks of C+D. There will also be 9 stacks of C+A and 999 stacks of C+B.

The stacks are separated in the following way:

First of all, stacks of different size induce different light output. The power scattered from an object trapped in the sensing element is proportional to the radius to the power of 6. The power scattered from a stack C+A+D, can hence easily be separated from a stack C+B. In a similar way, signals induced by change in refractive index will be dependent of the size of the trapped object. Their sizes differ, and they induce different light output. Secondly, we can locate the particles in two dimensions. So, if new bright spots appear between reaction 1 and 2, we know that these can not represent capture events of molecules A. The basic idea is illustrated on the right side of FIG. 2.

FIG. 2 thus illustrates the two chemical and optical detection steps that will increase specificity. Dashed circles mark the targeted molecules A. After the first chemical reaction, the captured particles may be detected as bright spots appearing on the image of the biosensor. The problem is that only a small part of these bright spots represents target molecules A. However, after the second chemical step, most of type A molecules become much more bright compared to the rest of the spots, as tag molecules D attach to the target. If molecule A and B are the same size, there may be some false positives, but since in general will be very small, the specificity is significantly increased.

Thus the captured target molecules may be found by looking for the brightest spots in the images, but also by comparing the images after the first capture and the second capture so as to detect the spots experiencing an increased illumination in both reactions.

A specific example of such possible two-step detection procedure is the detection of human interferon gamma (IFN-γ) where the capture detection antibody pair consists of Mouse anti-human IFN-γ (capture) and biotinylated goat anti-human IFN-γ (detection), as applied in sandwich ELISA. By applying monoclonal and polyclonal capture and detection antibodies, the sensitivity and specificity of the device can be further adjusted as monoclonal antibodies assure higher specificity, while polyclonal antibodies increase the sensitivity. Polyclonal and monoclonal antibodies may also be combined, by using e.g. monoclonal capture antibodies to ensure high specificity of the capture step, and polyclonal detection antibodies to ensure sensitive detection of the captured antigens. Such procedures are common within sandwich ELISA.

To summarize the invention relates to a method and system for detecting target molecules using an optical sensor element comprising a photonic crystal constituted by a membrane of a chosen transparent material, and more specifically the membrane being provided with a number of defined openings in a chosen pattern, the pattern being adapted to provide resonance at a chosen wavelength or range of wavelengths. The method including the following steps:

a) in a chosen number of said openings providing a capture molecules C having a high affinity to said target molecules A, b) moving a first fluid flow containing target molecules A through said openings, c) moving a second fluid flow containing a second reactant D being different from said capture molecules C but having a high affinity for the target molecules but a low affinity for other possible molecules in said first flow, d) illuminating said sensor element at said chosen wavelength thus obtaining a resonance and providing an image of said sensor element from a position outside the sensor element plane so as to detect light leaking from the resonator, and e) analyzing said image so as to detect the captured molecules as well as the reactant having reacted with them.

For comparison a step b1) may be included after step b) above where the sensor element is illuminated at said chosen wavelength thus obtaining a resonance and providing an image of said sensor element from a position outside the sensor element plane so as to detect light leaking from the resonator and thus detecting the captured molecules as we as the reactant having reacted with them. The analysis may then include an analysis in step e) includes a comparison between the images from step b1) and step d). The detection of a target molecule may then be registered when an increase in the induced signal in one position is detected in the resulting images in both steps b1) and d) as the combination of molecules C, A and D will be larger than the C and B combination.

In order to increase the sensitivity the reactant in step c) may be constituted by a large molecule chosen so as to maximize the induced signal in the photonic crystal.

In all of these cases the analysis in step e) may include deter a ion of the points in image having the highest intensity.

The system according to the invention is related to detecting target molecules using an optical sensor element comprising a photonic crystal constituted by a membrane of a chosen transparent material, being provided with a number of defined openings in a chosen pattern. A chosen number of said openings providing capture molecules having a high affinity to said target molecules. The pattern being adapted to provide resonance at a chosen wavelength or range of wavelengths as described in the abovementioned WO2010/0108952.

The system also comprises fluid conducting means for moving a first fluid flow containing target molecules through said openings, where the fluid conduction means also being adapted to, after conducting said first fluid flow conducting a second fluid flow containing a second reactant being different from said capture molecules but having a high affinity for the target molecules but a low affinity for other possible molecules in said first flow.

In addition illuminating means is used for illuminating said sensor element at said chosen wavelength thus obtaining a resonance and imaging means for providing an image of said sensor element from a position outside the sensor element plane so as to detect light leaking from the resonator.

The included analyzing means provides an analysis of said image so as to detect the captured molecules as well as the reactant having reacted with them. This analysis may comprise a detection of the induced points in the sensor element having the highest intensity, i.e. being above a predefined threshold, and/or a comparison between images taken after the first and second fluid for detecting the point having increased induced signal after both steps, indicating that molecules A is captured from the first fluid in the first step and molecule D was captured from the second fluid, indicating which of the points from the first picture that represents the target molecule.

It is also possible to introduce several additional steps to identify the number of other bindings, i.e. introduce an additional step with a third reactant E with a high affinity for B. Or, the additional steps may contain several reactants suitable for recognizing specific parts of nucleic acids or sequencing of such. In example, a specific part of a nucleic acid may be captured in one position, and then tagged with several reactants in sequence, enabling us to read out the capture of each of these reactants.

Between the chemical step 1 and the chemical step 2, an additional chemical step may be introduced. This additional step may block the capture molecule C for further reactions or disable the capture molecule C for further reactions. The purpose of this additional step is to reduce the likelihood for D to bind directly to C.

The second step may also include other methods for tagging that are suitable for imaging or spatial detection, like fluorescence, Raman, magnetic particles, radioactive tags and other methods may be applied.

The second step may also be a part of an amplification step. The purpose is to generate or induce a second signal that can be used to increase the specificity. In the case of a nucleic acid i.e. DNA or mRNA, an amplification step like the ones used in PCR or NASBA (or other amplification methods), can be used to increase the signal. The second step may also use a tag that enables polymerization or other methods that increase the signal response.

The specificity may be further increased by modifying pH, temperature or introducing chemical means to release the captured molecules. The release condition and the release time will give further information suitable to identify the target molecule, and monitoring of these will thereby increase the specificity.

The specificity may be further increased by modifying pH, temperature or introducing chemical means to modify the structure of the captured molecules, in example stretch out a nucleic acid or make it contract. The modification condition and the modification time will give further information suitable to identify the target molecule, and monitoring of these will thereby increase the specificity. Since the captured target molecule is not released in this case, several iterations of modifications may be performed.

The invention claimed is:

1. A method for detecting target molecules using an optical sensor element comprising a photonic crystal constituted by a membrane of a chosen transparent material, and more specifically the membrane being provided with a number of defined openings in a chosen pattern, the pattern being adapted to provide resonance at a chosen wavelength or range of wavelengths, the method including the following steps:
   a) in a chosen number of said openings providing a capture molecules having a high affinity to said target molecules;
   b) moving a first fluid flow containing target molecules through said openings;
   b1) wherein said sensor element is illuminated at said chosen wavelength thus obtaining a resonance, and providing a first image of said sensor element from a position outside the sensor element plane so as to detect light leaking from the resonator at the target molecule position;
   c) moving a second fluid flow containing a second reactant being different from said capture molecules but having a high affinity for the target molecules but a low affinity for other possible molecules in said first flow;
   d) illuminating said sensor element at said chosen wavelength thus obtaining a resonance and providing a second image of said sensor element from a position outside the sensor element plane so as to detect light leaking from the resonator; and
   e) an analyzing step including a comparison of said images provided in steps b1) and d), wherein the detection of a target molecule is registered when an increase in the induced signal in one position is detected in the resulting images in both steps b1) and d).

2. The method according to claim 1, wherein said reactant in step c) is constituted by a large molecule adapted to maximize the induced signal in the photonic crystal.

3. The method according to claim 1, wherein said analysis in step e) includes a determination of the points in the image having the highest intensity.

4. A system for detecting target molecules using an optical sensor element comprising a photonic crystal constituted by a membrane of a chosen transparent material, being provided with a number of defined openings in a chosen pattern, a chosen number of said openings providing a capture molecules having a high affinity to said target molecules, the pattern being adapted to provide resonance at a chosen wavelength or range of wavelengths, the system comprising:
   fluid conducting means for moving a first fluid flow containing target molecules through said openings;

the fluid conduction means also being adapted to, after conducting said first fluid flow conducting a second fluid flow containing a second reactant being different from said capture molecules but having a high affinity for the target molecules but a low affinity for other possible molecules in said first flow;

illuminating means for illuminating said sensor element at said chosen wavelength thus obtaining a resonance and imaging means for providing an image of said sensor element from a position outside the sensor element plane so as to detect light leaking from the resonator, the illumination and imaging means being adapted to provide images of the sensor element after the application of each fluid flow; and analyzing means for analyzing said image provided after each fluid flow, so as to detect the captured molecules as well as the reactant having reacted with them based on the difference between said images, wherein said analyzing means is adapted to register a target molecule when detecting an increase in the induced signal in a position between the image provided after the first fluid flow to the image provided after the second fluid flow.

5. The system according to claim 4, wherein said reactant in said second fluid flow is constituted by a large molecule adapted to maximize the induced signal in the photonic crystal.

6. The system according to claim 4, wherein said analysis includes a determination of the points in the image having an intensity over a certain predefined threshold.

* * * * *